United States Patent [19]
Jarvik

[11] Patent Number: 5,904,646
[45] Date of Patent: May 18, 1999

[54] INFECTION RESISTANT POWER CABLE SYSTEM FOR MEDICALLY IMPLANTED ELECTRIC MOTORS

[76] Inventor: Robert Jarvik, 333 W. 52nd St., 15th Floor, New York, N.Y. 10019

[21] Appl. No.: 08/925,939

[22] Filed: Sep. 8, 1997

[51] Int. Cl.⁶ ..................................................... A61M 1/12
[52] U.S. Cl. ............................................... 600/16; 623/3
[58] Field of Search ................... 607/1, 116; 600/16–18; 623/3; 604/174, 175; 128/897, 899, DIG. 3

[56] References Cited

U.S. PATENT DOCUMENTS

| | | | |
|---|---|---|---|
| 2,917,751 | 12/1959 | Fry et al. | 623/3 |
| 3,771,173 | 11/1973 | Lamb, Jr. | 623/3 |
| 3,923,060 | 12/1975 | Ellinwood, Jr. | 128/DIG. 1 |
| 4,925,443 | 5/1990 | Heilman et al. | 600/16 |
| 5,464,446 | 11/1995 | Dreessen et al. | 607/116 |
| 5,507,303 | 4/1996 | Kuzma | 128/899 |

*Primary Examiner*—William E. Kamm
*Assistant Examiner*—George R. Evanisko

[57] ABSTRACT

Implanted medical devices such as heart assist devices powered by electric motors or solenoids require a high amount of power compared to other electric implants such as pacemakers which do not use motors. A percutaneous power transmission system for use with implanted motors includes a skull-mounted post and a highly flexible array of wires implanted in a serpentine configuration to enhance flex life and prevent failure due to excessive longitudinal tension. In the preferred embodiment, a cable passed across the neck in zig-zag fashion includes a separable implanted connector removably attachable within a post fixed by bone screws and a flange to the skull. The implanted connector is passed through smaller incisions and a smaller subcutaneous tunnel then would be required to fit the flange. This reduces surgical trauma, and facilitates healing without infection and with minimal scarring on the neck.

13 Claims, 2 Drawing Sheets

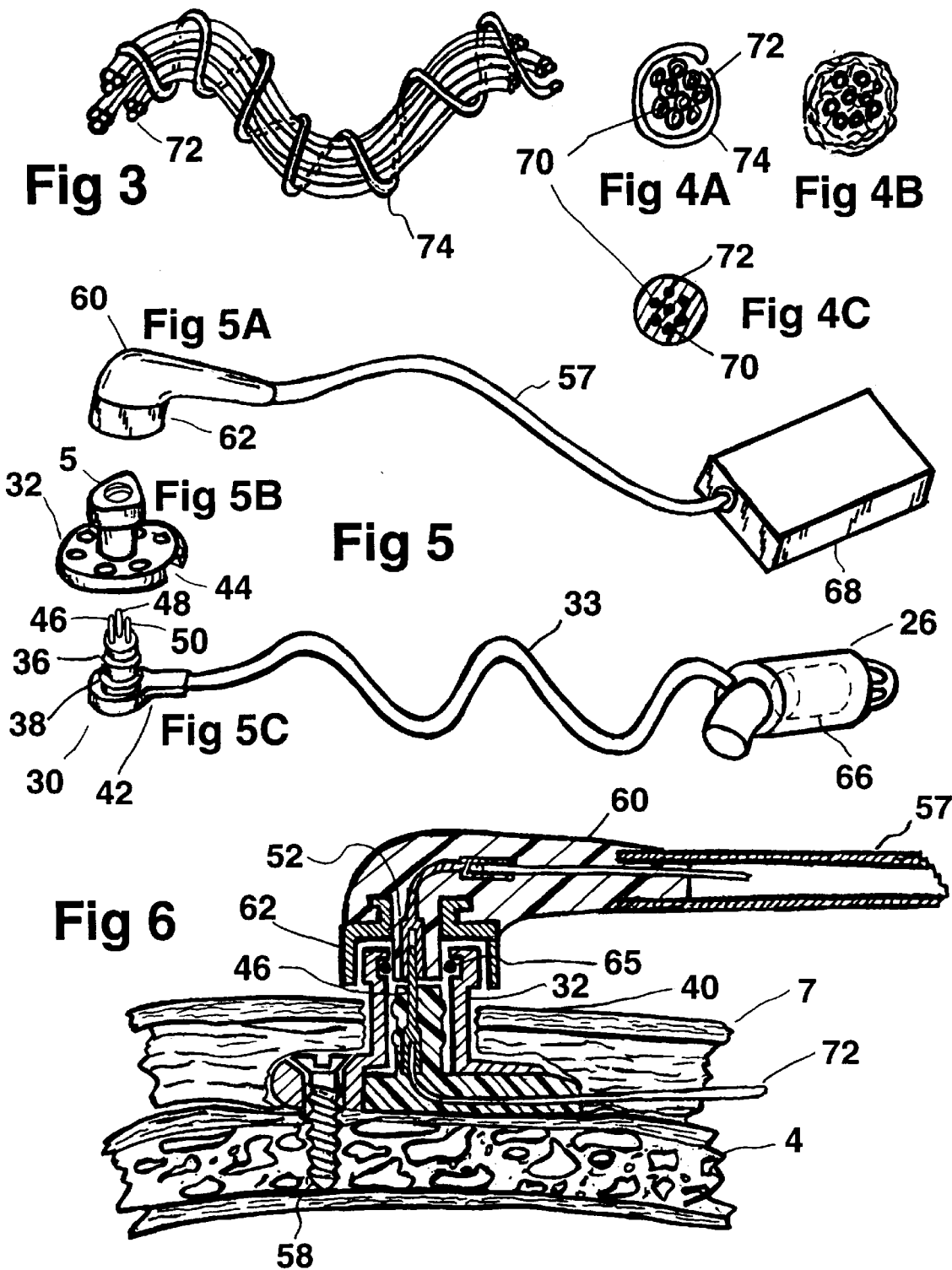

INFECTION RESISTANT POWER CABLE SYSTEM FOR MEDICALLY IMPLANTED ELECTRIC MOTORS

BACKGROUND OF THE INVENTION

Many medical devices which utilize electric power have been developed for long term implantation. If the power required is low enough—such as with pacemakers, and various types of muscle and nerve stimulators, implanted batteries can reliably store enough energy for years of operation. These may utilize tiny amounts of power measured in milliamps using intermittent brief bursts of stimulation. Devices such as blood pumps, heart assist devices or total artificial hearts operate continuously and require thousands of times as much energy as pacemakers. A battery which powers a pacemaker for a decade would power an artificial heart for less than an hour.

Percutaneous leads are means of accessing the tissues beneath the skin. Many types of percutaneous leads have been developed and include catheters for fluid access, fabric-covered pneumatic tubes, and electric cables with large subcutaneous flanges for soft tissue ingrowth to fix the device in place and provide a barrier to bacterial infections. The effectiveness of most of these devices is limited.

A major cause of infection of percutaneous leads is trauma to the tissues where the device penetrates the skin. Motion of the tube or cable relative to the skin tears the cellular junction of the body tissue to the prosthetic material. This occurs repeatedly—prevents tight healing and permits bacteria to enter.

The most successful type of percutaneous lead developed to date uses rigid fixation to bone to prevent motion of the device and places the device in a position where virtually no motion of the skin over the bone occurs. This protects the junction of the skin and percutaneous lead from trauma. Skull-mounted devices of this type have proven highly effective (greater than 95% 10 year success) in hundreds of artificial hearing cochlear implant patients. The longest implant to date is 20 years and the patient continues to do well. In addition to excellent stabilization on the skull, the tissues of the scalp are highly vascular and adapted to resist wound infection, as an evolutionary mechanism to protect the brain.

For providing power to an artificial heart or assist device located in the chest, the skull-mounting position has the major disadvantage that wires must be tunneled through the tissues of the neck, and must withstand a great deal of flexing and torsional strain as the patient bends and turns the head and neck.

Tunneling to pass the cable through the neck tissues and across the chest wall to reach the heart involves trauma which should be minimized. A large-diameter flange is needed to achieve strong fixation of the percutaneous lead device to the skull, but is not compatible with minimizing trauma during tunneling. Excessive trauma can cause scarring, which may be cosmetically unfavorable, and can also result in infection. Additionally, in order to relieve strain on the cable, we have developed a method which utilizes a serpentine cable having several zig-zag loops as the cable lies along the neck. This requires several incisions which should be as small as possible.

For these and other reasons, the device of the present invention provides a power cable and connector part which is separable from the large diameter flange and is then attached to the flange after tunneling. This permits zig-zag tunneling with minimal trauma. A keyed configuration of the pedestal and connector is provided which permits the patient to safely plug and unplug the connector on the back or side of the head without seeing it.

OBJECTS OF THE INVENTION

It is an object of the invention to provide means of bringing electric power across the skin to an implanted electrical device which will function safely without serious infection for more than a decade.

It is another object of the invention to provide a bone-mounted percutaneous lead having a removable electric connector.

It is a further object of the invention to provide a percutaneous lead and electric cable system capable of withstanding the normal motion of the neck while maintaining the strain on the electric wires low enough for reliable long term use.

It is a still further object of the invention to provide a method of implanting electric cables in the neck to prevent tension on the wires or on the junction of the wires to the percutaneous lead.

Another object of the invention is to provide a connector integrated with bone mounted fixation means—such that a cable external to the patient can be connected to an internal cable and in the event of damage the external cable can be changed.

Another object of the invention is to provide a skull-mounted electrical connector which the patient can safely disconnect and reconnect on the back of the head, without being able to see it.

Another object of the invention is to provide a robust percutaneous lead system resistant to damage in the event of trauma—such as a skull mounted device which is not damaged if the patient bumps it when getting into a car.

An additional object of the invention is to provide a highly flexible power cable having low electrical resistance to enhance the efficiency of devices using implanted electric motors.

THE DRAWINGS

FIG. 3 is a perspective drawing showing a bundle of individually insulated wires surrounded by a coil which retains them together.

FIG. 4A is a cross-sectional view of a bundle of nine wires retained together by a coil of absorbable material.

FIG. 4B is a cross-sectional view of the cable of FIG. 4A enclosed in a capsule of connective tissue following implantation in the body and absorption of the coil.

FIG. 5 is an exploded assembly view of the device showing: at 5A the external connector, at 5B the skull-mounted post and flange, and at 5C the internal portion of the connector and cable.

FIG. 6 is a longitudinal sectional view of the three parts shown in FIG. 5 taken at plane 6—6 of FIG. 2, also showing the attachment of the flange to the skull and the post penetrating a hole in the skin.

SPECIFIC DESCRIPTION OF THE INVENTION

Figure 1:
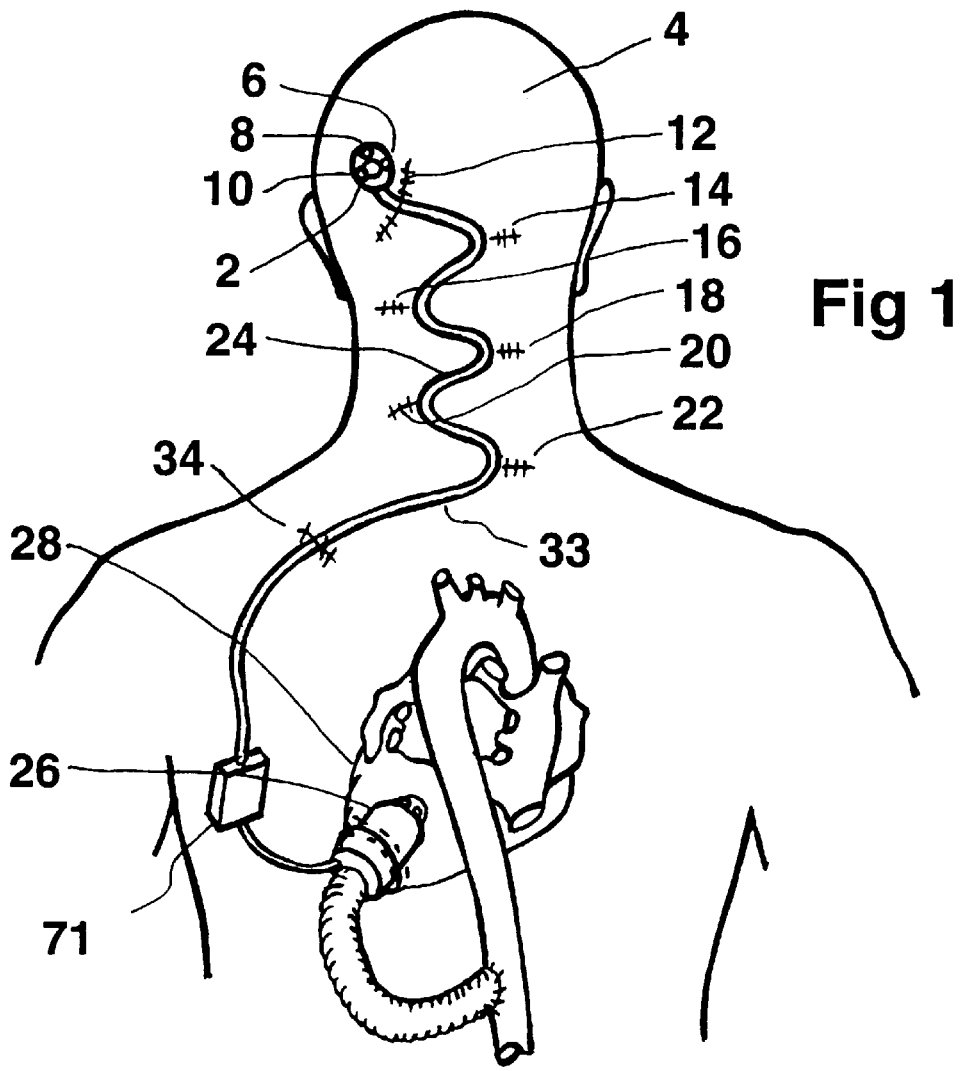
FIG. 1 is an illustration of a patient viewed from the back generally showing the skull-mounted post, wires across the neck, and showing an intraventricular artificial heart in the chest.
Figure 2:
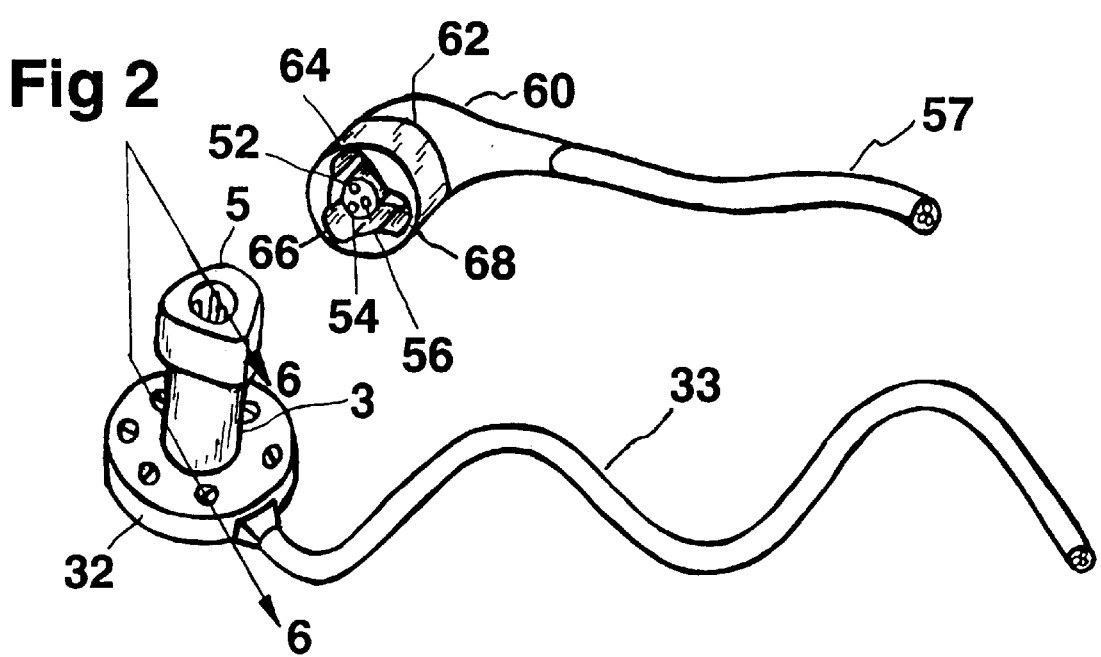
FIG. 2 is a three dimensional view of the skull-mounted post with the implanted part of the connector assembled into it and the external cable connector shown separated.

Referring to FIGS. 1 & 2, the implanted components of the preferred embodiment are shown. A post 3 having a flange 2 is mounted to the skull 4 by bone screws 6, 8, 10 in a position on the side and back of the head behind the ear. A relatively large incision 12 is used to create a pocket into which the flange is inserted and attached to the skull with screws. The position of the incision which creates the pocket is selected so that most blood vessels to the area of the skin where the post is exited through a separate punched hole are not cut. This method, developed for artificial hearing pedestals, is described in the literature by Parkin and others and has proven highly effective at preventing skin necrosis. A series of small skin incisions 14, 16, 18, 20, 22 placed in staggered fashion down the neck are used to implant an internal cable 24 so that it assumes a serpentine curvature as it lies in the subcutaneous tissues of the neck as illustrated. The cable is connected to an intraventricular blood pump 26 which is placed within the natural heart 28.

The cable is attached to the blood pump at one end and at the other end terminates at a connector 30 best illustrated in FIG. 5C. This connector is separable from the skull-mounted post and flange 32 best illustrated by FIGS. 5B & 5C.

The surgical procedure for implantation of the device to achieve the configuration shown in FIG. 1 is as follows:

The chest is first opened and the internal cable 33 together with the cable connector is tunneled from the inside of the chest cavity passing outward through a small incision 34 on the chest wall, either in back or laterally near the base of the neck. Using a tunneling instrument, the connector and cable is then sequentially passed from incision 34 to incision 22, from 22 to 20, from 20 to 18, from 18 to 16, from 16 to 14, and finally from 14 to 12. At each incision the connector is first brought out through the skin and then on the next step is reinserted into the same incision. In this way relatively short tunneling steps are made, which can be done safely with a straight or gently curved instrument. After the cable has been completely placed from the chest to the head the internal connector 30 is inserted into the post and flange part 32. The connector is composed of an elastic material with sealing protrusions 36, 38 which act like O-rings to seal the connector against a bore 40 within the post best seen in FIG. 6. Alternatively actual O-rings may be used. The internal connector incorporates a cable extension 42 which nests within a slot in the flange 44 and rotationally locates the connector contacts 46, 48, 50 in the proper position to mate with corresponding contacts 52, 54, 56 on the external cable 57 best seen in FIG. 2. The flange is then affixed to the skull 4 by bone screws, one of which 58 is best seen in FIG. 6. Thus, the implanted connector is confined between the skull and the flange and is retained in position.

After the flange is screwed to the skull 4 the post is brought through the skin 7 through a hole preferably cut with a cylindrical knife. The skin incisions are sutured. The external cable connector is then attached to the external power source 68 which may include batteries or another electric power source, and the connection is complete.

FIG. 5A shows the external connector 60. A sleeve 62 having an asymmetrical cutout designed to mate with the shaped end of the post 5 is structured so that it can only fit over the post in one rotational position. If the connector contacts used are pins, as illustrated in the preferred embodiment, the pins are recessed within the post so that they cannot be damaged or bent by attempts to push the external connector over the post when the connector ports are not properly aligned. A mechanism to hold the external connector to the post by spring forces is provided. Referring to FIG. 2, the sleeve 62 is seen to have a generally triangular shaped cutout with three thin walled portions 64, 66, 68 located approximately 120 degrees apart. The sleeve is manufactured from a metal such as stainless steel or titanium alloy. After the triangular cutout is completed, the sleeve is placed in a clamping device such as a three jaw chuck which applies force to each of the three thin wall portions of the sleeve when the chuck is tightened. Sufficient force is applied to bend the sleeve beyond its elastic limit and deform it. In the shape it assumes when the sleeve is pushed over the post, spring contact is achieved at the three vortices of the shaped tip of the post. This spring force removably attaches the external connector to the post. Alternatively, slots may be cut in the sleeve to increase the motion of tongue like portions of it that are thus formed and better adapt the sleeve to act as a spring clamping device which holds the external cable to the post.

An O-Ring seal 65 best seen in FIG. 6, isolates the connector contacts from fluid entry along the junction between the external connector and the post. Since the internal connector port is also isolated from fluid entry to the area of the contacts by a seal against the bore within the post, no fluid can reach the contacts. Thus the connector is waterproof, permitting the patient to safely bathe.

The cables which traverse the neck must withstand years of flexing and torsional stress. In many applications, coiled cables such as used with telephone receiver cord provide very long term durability. However, when placed subcutaneously in the neck, the cable should be as small in diameter as possible. The present invention utilizes a bundle of many small cables to achieve both high flexibility and redundancy. In the preferred embodiment the motor is within the heart and is a three phase brushless DC motor 66 powered from an external battery and control system 68. The three-phase motor requires a minimum of three wires, one for each phase. In the present invention, multiple wires are used with three individual cables for each phase—thus a total of nine cables in all. Each cable may be an array of many individual wires such as a 7×7 wire rope array as commonly used with cardiac pacemakers. FIG. 4A illustrates a power cable composed of nine smaller 7×7 cables, each individually insulated. A 7×7 configuration 70 is insulated by an extruded polymer coating 72. The bundle of nine 7×7 cables is surrounded by a coil of retaining material such as a stainless steel spring or a springlike coil of absorbable suture material 74. Such a coil may be formed by heat-setting a polymer monofilament over a mandrill. FIG. 3 illustrates a cable in which three bundled 7×7 cables are used for each motor phase. Providing two or more cables in parallel for each motor phase has the advantage that the resistance of the multiple cables is lower than the resistance of a single cable of the same size. This increases the motor/cable efficiency. If any one cable breaks the others provide redundancy to keep the motor running. Measurement of the resistance will reveal if any cable is broken.

As illustrated in FIGS. 3 and 4A, at the time of implant the bundle of cables is held together by an absorbable coil. After several weeks a fibrous tissue capsule forms, surrounding the bundle and retaining the individual strands together. After several months, the absorbable coil is reabsorbed by the body leaving a cable composed of a bundle of individual smaller cables surrounded by a fibrous tissue capsule. The capsule is flexible and permits the cables within it to freely flex. Thus the cable structure provides long-term power to the motor reliably for many years. An alternative cable is composed of a bundle of individually insulated wires or cables. These are braided to retain them together during surgical implantation. A tissue capsule will then form around them further retaining the bundle within the body.

In other embodiments of the invention, the cables may provide DC power to an implanted control system 71 or to charge an internal battery which may be implanted in conjunction with or within the control system 71. In such a configuration only two wires are needed, but a bundled cable with redundancy is still desirable.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. An infection-resistant percutaneously powered electric actuator comprising:
   a. an implantable electric motor,
   b. an external power supply,
   c. electric conductor means, comprising a plurality of wires adapted for external and internal use in a patient's body, for conducting power to said implantable electric motor from said external power supply,
   d. separable mating electric contact means for establishing electric conduction when mechanically brought together, affixed to said wires between said motor and said power supply,
   e. tube means for containing said electric contact means,
   f. flange means for attaching said tube means to a bone within said patient's body, and,
   g. electric connector means for removably aligning and retaining said electric contact means to connect or disconnect said motor to said power supply.

2. The electric actuator system of claim 1 further comprising one of a helically wound metal spring or polymer spring for surrounding said wires in said body and for retaining together said wires as a bundle in said body.

3. The electric actuator system of claim 2 further comprising an internal blood pump implantable in the body and connected to said electric motor and wherein said bundle of wires are adapted for transversing the neck of said patient.

4. The electric actuator system of claim 1 wherein said wires in said patient's body are braided to retain said wires together.

5. The electric actuator system of claim 4 further comprising an internal blood pump implantable in the body and connected to said electric motor and wherein said braided wires are adapted for transversing the neck of said patient.

6. The electric actuator system of claim 1 wherein said electric conductor means further comprises redundant wires for conducting power in parallel to each phase of said motor from said power supply.

7. The electric actuator system of claim 1 wherein said tube means and flange means are rigidly affixed together and include keyway means for removably retaining said connector means in proper rotational position for alignment of said contact means.

8. An infection-resistant percutaneously powered electric actuator comprising:
   a. an implantable electric motor,
   b. an external power supply,
   c. electric conductor means, comprising a plurality of separately insulated wires for conducting power to said implantable electric motor from said external power supply,
   d. tube means for retaining part of said electric conductor means, and through which said conductor means may traverse the skin of a patient,
   e. flange means for attaching said tube means to a bone within a patient's body, and one of a helically wound metal spring or polymer spring for surrounding said wires in said body and for retaining together said wires as a bundle in said body.

9. The electric actuator system of claim 8 wherein said electric conductor means further comprises redundant wires for conducting power in parallel to each phase of said motor from said power supply.

10. The electric actuator system of claim 8 further comprising an internal blood pump implantable in the body and connected to said electric motor and wherein said bundle of wires is adapted for transversing the neck of said patient.

11. An infection-resistant percutaneously powered electric actuator comprising:
    a. an implantable electric motor,
    b. an external power supply,
    c. electric conductor means, comprising a plurality of separately insulated wires, for conducting power to said implantable electric motor from said external power supply,
    d. tube means for retaining part of said electric conductor means, and through which said conductor means may traverse the skin of a patient,
    e. flange means for attaching said tube means to a bone within a patient's body and wherein said wires within said body are braided together to form a cable.

12. The electric actuator system of claim 11 wherein said electric conductor means further comprises redundant wires for conducting power in parallel to each phase of said motor from said power supply.

13. The electric actuator system of claim 11 further comprising an internal blood pump implantable in the body and connected to said electric motor and wherein said cable of wires is adapted for transversing the neck of said patient.

\* \* \* \* \*